(12) United States Patent
Goudet

(10) Patent No.: US 11,771,730 B2
(45) Date of Patent: Oct. 3, 2023

(54) COMBINATION OF RHODIOLA AND ASTRAGALUS FOR THE TREATMENT OF NEURODEGENERATIVE DISEASES

(71) Applicant: HUMAN BY NATURE, Toulouse (FR)

(72) Inventor: Gérald Goudet, Fiac (FR)

(73) Assignee: HUMAN BY NATURE, Toulouse (FR)

( * ) Notice: Subject to any disclaimer, the term of this patent is extended or adjusted under 35 U.S.C. 154(b) by 48 days.

(21) Appl. No.: 16/969,410

(22) PCT Filed: Feb. 15, 2019

(86) PCT No.: PCT/FR2019/050342
§ 371 (c)(1),
(2) Date: Aug. 12, 2020

(87) PCT Pub. No.: WO2019/158870
PCT Pub. Date: Aug. 22, 2019

(65) Prior Publication Data
US 2021/0052683 A1    Feb. 25, 2021

(30) Foreign Application Priority Data

Feb. 15, 2018 (FR) .................................. 1851298
Feb. 16, 2018 (FR) .................................. 1851319

(51) Int. Cl.
| | | |
|---|---|---|
| *A61K 36/41* | (2006.01) | |
| *A61K 31/7034* | (2006.01) | |
| *A61K 36/481* | (2006.01) | |
| *A61P 25/28* | (2006.01) | |
| *A61K 31/7028* | (2006.01) | |
| *A61K 31/7048* | (2006.01) | |

(52) U.S. Cl.
CPC .......... *A61K 36/41* (2013.01); *A61K 31/7034* (2013.01); *A61K 36/481* (2013.01); *A61P 25/28* (2018.01); *A61K 31/7028* (2013.01); *A61K 31/7048* (2013.01)

(58) Field of Classification Search
None
See application file for complete search history.

(56) References Cited

U.S. PATENT DOCUMENTS

| | | | |
|---|---|---|---|
| 2008/0081046 A1* | 4/2008 | Olalde .................. | A61K 36/07 424/769 |
| 2008/0118583 A1* | 5/2008 | Olalde Rangel ....... | A61K 36/00 424/728 |
| 2009/0110674 A1* | 4/2009 | Loizou .................. | A61K 36/00 424/94.2 |

FOREIGN PATENT DOCUMENTS

| | | | |
|---|---|---|---|
| CN | 1981857 A | * | 6/2007 |
| CN | 1981857 A | | 6/2007 |
| CN | 102940787 A | | 2/2013 |
| KR | 20030007105 A | | 1/2003 |

OTHER PUBLICATIONS

Huang (CN 1981857A, Aug. 12, 2020 IDS, machine translation of Description.*
Morgan, M., Bone, K., Rhodiola rosea—Rhodiola, Medi Herb—a phytotherapist's perspective, No. 47 Feb. 2005.*
"Héritez de la nature toute sa jeunesse . . ." or "Inherit from Nature all its Youth . . .", Composition d'ADN Téloméractives ©, (2017) http://www.adn-astragale.fr/astragale.
International Search Report received in PCT/FR2019/050342, dated May 16, 2019.
Nabavi et al., "*Rhodiola rosea* L. and Alzheimer's Disease: From Farm to Pharmacy", Phytotherapy Research, (2016), vol. 30, pp. 532-539.
Xia et al., "Neuroprotective Effects of Astragaloside IVon Parkinson Disease Models of Mice and Primary Astrocytes", Experimental and Therapeutic Medicine, (2017), vol. 14, pp. 5569-5575.
"Héritez de la nature toute sa jeunesse . . ." Composition d'ADN Téloméractives ©, (2017) http://www.adn-astragale.fr/astragale.
Haiyan et al., "Effect of Astragaloside IV on Neural Stem Cell Transplantation in Alzheimer's Disease Rat Models." Evidence-Based Complementary and Alternative Medicine. 2016. 8 pages.

* cited by examiner

*Primary Examiner* — H. Sarah Park
(74) *Attorney, Agent, or Firm* — ARENTFOX SCHIFF LLP

(57) ABSTRACT

The present invention relates to a product containing an extract of *Rhodiola* and an extract of *Astragalus* as products to be combined for simultaneous administration, separately or staggered over time, in the treatment of a neurodegenerative disease, and in particular for the treatment of Alzheimer's disease and Parkinson's disease.

12 Claims, 8 Drawing Sheets

COMBINATION OF RHODIOLA AND ASTRAGALUS FOR THE TREATMENT OF NEURODEGENERATIVE DISEASES

CROSS-REFERENCE TO RELATED APPLICATIONS

This application is a National Stage Entry of PCT/FR2019/050342, filed Feb. 15, 2019, which claims foreign priority to FR Patent Application No. 1851298, filed on Feb. 15, 2018 and FR Patent Application No. 1851319, filed on Feb. 16, 2018, the disclosures of which are hereby incorporated by reference in their entireties.

The present invention relates to the use of an extract of *Rhodiola* and of an extract of *Astragalus* to treat neurodegenerative diseases, and more particularly diseases such as Alzheimer's or Parkinson's.

By "degenerative diseases" is meant all pathologies which advance progressively towards development of deficiencies and damage in the patient. Generally of genetic origin, degenerative diseases may also be caused by massive exposure to substances that are biological and toxic.

By "neurodegenerative disease" is meant a disease which progressively affects the functioning of the nervous system. Generally, the functioning of the nerve cells, and more particularly of the neurons, becomes altered. These diseases develop at different rates and are often irreversible.

More particularly, by neurodegenerative diseases is meant the following diseases: Alzheimer's disease, Parkinson's disease, Huntington's disease, amyotrophic lateral sclerosis, dementia with Lewy bodies, Pick's disease, progressive supranuclear palsy, multiple sclerosis, human or animal prion diseases for example such as bovine spongiform encephalopathy, and myopathy.

On account of the increase in life expectancy, the giving of diagnoses of neurodegenerative diseases such as Alzheimer's disease or Parkinson's disease, is constantly on the rise.

Rare before the age of 65, Alzheimer's disease is a disease characterized by progressive degeneration of the neurons, leading little by little to the loss of intellectual functions: in a first phase this involves in particular memory impairment, impairment of executive functions and problems of orientation in time and space. The progressive development of the disease in the patient leads to the irreversible installation of dementia.

Rare before the age of 45, Parkinson's disease affects approximately 1% of people over the age of 65. This disease, of which the development is just as progressive and irreversible as for Alzheimer's disease, is characterized by the destruction of a particular population of the neurons. It induces so-called "motor" symptoms such as slowness of performance and coordination of movements, excessive rigidity of the muscles and trembling, and "non-motor" symptoms such as cognitive impairment, sleep impairment, loss of balance and/or depression.

None of the drugs currently prescribed for these two diseases enables them to be cured or to stop their development. They are principally directed to delaying the development of the diseases and attempt to treat their symptoms.

The work of the inventors has made it possible to show that a new combination of active ingredients enabled neurodegenerative diseases to be treated, in particular diseases such as Alzheimer's or Parkinson's.

The invention thus concerns a product containing an extract of *Rhodiola* and an extract of *Astragalus* as combined products for use that is simultaneous, separate or spread overtime in the treatment of a neurodegenerative disease.

It also relates to the combination of an extract of *Rhodiola* and of an extract of *Astragalus* for use in the treatment of a neurodegenerative disease.

By "an extract of *Rhodiola*" is meant an extract or a mixture of extracts of *Rhodiola*.

By "an extract of *Astragalus*" is meant an extract or a mixture of extracts of *Astragalus*.

As is shown in Example 2, the combination of an extract of *Rhodiola* and of an extract of *Astragalus* has a synergistic curative effect in the context of a neurodegenerative disease model.

Furthermore, as shown in Example 3, the combination of an extract of *Rhodiola* and of an extract of *Astragalus* also has a preventive protective effect in the context of the same neurodegenerative disease model.

More particularly, the neurodegenerative disease is chosen from the group consisting of Alzheimer's disease, Parkinson's disease, Huntington's disease, amyotrophic lateral sclerosis, prion diseases for example such as bovine spongiform encephalopathy, dementia with Lewy bodies, Pick's disease and myopathy.

Preferably, it is a disease selected from the group consisting of Alzheimer's disease, Parkinson's disease, Huntington's disease, amyotrophic lateral sclerosis, bovine spongiform encephalopathy and myopathy and more preferably, Alzheimer's disease, Parkinson's disease, Huntington's disease and myopathy.

More particularly, it is a disease selected from the group consisting of Alzheimer's disease and Parkinson's disease.

As a matter of fact, the inventors have shown that a combination of extracts of *Rhodiola* and of *Astragalus* made it possible not only to maintain the length of the neurites in a neurodegenerative disease model, in particular of Alzheimer's disease, but also to procure their elongation. This result is surprising since an extract of *Rhodiola* or of *Astragalus* alone does not enable the length of the neurites to be improved in a neurodegenerative disease model and possibly even deteriorates it.

The use of the product may be simultaneous, separate or spread over time.

By way of example, the product may be administered via a single dose (tablet, capsule, etc.) comprising an extract of *Rhodiola* and an extract of *Astragalus* or via two separate doses, a first dose comprising an extract of *Rhodiola* and a second dose comprising an extract of *Astragalus*. In this second case, the two doses may be administered simultaneously, separately or spread over time.

Advantageously, the combined products, i.e. the extract of *Rhodiola* and the extract of *Astragalus*, are used simultaneously.

The product containing an extract of *Rhodiola* and an extract of *Astragalus* as combined products may be used for a preventive and/or curative treatment.

As is shown in Examples 2 and 3, the combined products according to the invention have shown a preventive and curative effect in the context of a neurodegenerative disease model and more particularly in the context of a model of Alzheimer's disease.

Preferably, the product containing an extract of *Rhodiola* and an extract of *Astragalus* as combined products is used for a curative treatment of neurons, in particular in the context of Alzheimer's disease.

More particularly, the curative treatment of neurons is made in particular by elongation of the neurites of said neurons.

Advantageously, in the product containing an extract of *Rhodiola* and an extract of *Astragalus* as combined products, the ratio by dry weight of the extract of *Astragalus* relative to the extract of *Rhodiola* is comprised between 0.5 and 1.5.

It will be noted that, in the context of the present application, and unless otherwise stipulated, the ranges of values indicated are understood to be inclusive.

Preferably, the ratio by dry weight of the extract of *Astragalus* relative to the extract of *Rhodiola* is comprised between 0.8 and 1.2, preferably of the order of 1.

Advantageously, the extract of *Rhodiola* is an extract of *Rhodiola rosea*.

Preferably, the product containing an extract of *Rhodiola* and an extract of *Astragalus* as combined products comprises a dose of at least 50 mg/day of an extract of *Rhodiola*, said extract being an extract of *Rhodiola rosea*.

More particularly, for an adult human, the dose of extract of *Rhodiola rosea* may be comprised between 50 and 500 mg/day, more preferably between 100 and 250 mg/day, still more preferably of the order of 150 mg/day.

More generally, for an animal, the product containing an extract of *Rhodiola* and an extract of *Astragalus* as combined product may comprise a dose of dry extract of *Rhodiola rosea* of at least 0.5 mg/kg/day, preferably a dose comprised between 1 and 10 mg/kg/day, for example of the order of 1.5 to 2 mg/kg/day.

Preferably, these doses are doses of dry extracts.

Preferably, the extraction is made from powder of *Rhodiola rosea* roots.

*Rhodiola rosea*, also called golden root or arctic root, is a perennial plant of the Crassulaceae family, which grows mainly in the cold regions of the world, such as the cold regions of Asia, Siberia, North America and the mountainous regions of Europe (the Alps, the Pyrenees, the Carpathians, Scandinavia, Iceland, Great Britain and Ireland). This plant is used, particularly in traditional Chinese medicine, to combat stress and mood disorders. Advantageously, *Rhodiola rosea* comes from Asia, preferably from China.

Advantageously, the extract of *Rhodiola rosea* roots is a hydroalcoholic extract. Typically, the extraction solvent for the extract is a water-ethanol mixture, such as a water-ethanol mixture comprising at least 50% by volume, preferably at least 60% by volume, for example such as 70% by volume of water.

Advantageously, the weight ratio of water-ethanol mixture to powder of *Rhodiola rosea* roots is between 16:1 and 4:1, preferably between 12:1 and 6:1, such as of the order of 10:1 to 8:1.

The extraction of *Rhodiola* can be carried out according to the usual methods (percolation, infusion, decoction, maceration) well known to the person skilled in the art. Preferably, the extraction of the powder is repeated several times. Advantageously, the extraction is carried out hot, preferably at a moderate temperature (40 to 100° C.). After extraction, the extract is preferably dried.

Advantageously, the extract of *Rhodiola rosea* contains at least 1.5% by weight of rosavin with respect to the total weight of dry extract of *Rhodiola rosea*.

Rosavin designates a glycoside of cinnamic alcohol, extracted from *Rhodiola*, and more particularly from *Rhodiola rosea*.

Preferably, the extract of *Rhodiola rosea* comprises at least 2% by weight of rosavin, more preferably at least 2.5% by weight of rosavin, still more preferably at least 3% by weight of rosavin, with respect to the total weight of dry extract of *Rhodiola rosea*.

Advantageously, the *Rhodiola rosea* extract also comprises at least 0.25% by weight of salidroside, with respect to the total weight of dry extract of *Rhodiola rosea*.

Salidroside (also called "rhodioloside") designates a phenylpropanoid glucoside, extracted from *Rhodiola*, and more particularly from *Rhodiola rosea*.

Preferably, the extract of *Rhodiola rosea* comprises at least 0.5% by weight of salidroside, more preferably at least 0.75% by weight of salidroside, still more preferably at least 1% by weight of salidroside, with respect to the total weight of dry extract of *Rhodiola rosea*.

More particularly, the *Rhodiola rosea* extract comprises at least 1.5% by weight of rosavin and at least 0.25% by weight of salidroside, preferably at least 2% by weight of rosavin and at least 0.5% by weight of salidroside, more preferably, at least 2.5% by weight of rosavin and at least 0.75% by weight of salidroside, still more preferably at least 3% by weight of rosavin and at least 1% by weight of salidroside, with respect to the total weight of dry extract of *Rhodiola rosea*.

The *Rhodiola* extract, and more particularly the *Rhodiola rosea* dry extract, may also advantageously contain rosarin and/or rosin.

As mentioned above, the *Rhodiola* extract is used in combination with an *Astragalus* extract.

Advantageously, the extract of *Astragalus* is an extract of *Astragalus membranaceus*.

Preferably, the product containing an extract of *Rhodiola* and an extract of *Astragalus* as combined products comprises at least a dose of 50 mg/day of an extract of *Astragalus*, said extract being an extract of *Astragalus membranaceus*.

More particularly, for an adult human, the dose of extract of *Astragalus membranaceus* can be between 50 and 500 mg/day, more preferentially between 100 and 250 mg/day, still more preferentially of the order of 150 mg/day.

More generally, for an animal, the product containing an extract of *Rhodiola* and an extract of *Astragalus* as combined products may comprise a dose of dry extract of *Astragalus membranaceus* of at least 0.5 mg/kg/day, preferably a dose comprised between 1 and 3 mg/kg/day, for example of the order of 1.5 to 2 mg/kg/day.

Preferably, these doses are doses of dry extracts.

Preferably, the extraction is carried out from powder of *Astragalus membranaceus* roots.

*Astragalus membranaceus*, also called *Astragalus penduliflorus* or *Astragalus propinquus*, is a plant of the Fabaceae family which grows in Asia, more particularly in northern China and in the provinces of Yunnan and Sichuan. This plant is used, particularly in traditional Chinese medicine, to stimulate the immune system and fight infections. Advantageously, the *Astragalus membranaceus* comes from Asia, preferably from China.

Advantageously, the extract of *Astragalus membranaceus* comprises at least 0.2% by weight of astragalosides with respect to the weight of dry extract of *Astragalus membranaceus*.

By astragalosides (sometimes designated "astrangaloside") is designated triterpene oligoglycosides, extracted from *Astragalus*, and more particularly from *Astragalus membranaceus*.

Preferably, the extract of *Astragalus membranaceus* comprises at least 0.4% by weight of astragalosides, more preferably at least 0.6% by weight of astragalosides, still more preferably at least 0.8% by weight of astragalosides, with respect to the total weight of dry extract of *Astragalus membranaceus*.

Advantageously, the extract comprises a mixture of astragalosides, that is to say at least two astragalosides selected from astragalosides I, II, III, IV, V, VI and VII.

Preferably, the extract contains a mixture of the 7 aforementioned astragalosides.

Advantageously, the extract of *Astragalus membranaceus* contains at least 10% by weight of polysaccharides, with respect to the total weight of dry extract of *Astragalus membranaceus*.

Preferably, the extract of *Astragalus membranaceus* comprises at least 12% by weight of polysaccharides, more preferably at least 14% by weight, still more preferably at least 16% by weight of polysaccharides with respect to the total weight of dry extract of *Astragalus membranaceus*.

More particularly, the extract of *Astragalus membranaceus* comprises at least 0.2% by weight of astragalosides and at least 10% by weight of polysaccharides, preferably, at least 0.4% by weight of astragalosides and at least 12% by weight of polysaccharides, more preferably, at least 0.6% by weight of astragalosides and at least 14% by weight of polysaccharides, still more preferably at least 0.8% by weight of astragalosides and at least 16% by weight of polysaccharides, with respect to the total weight of dry extract of *Astragalus membranaceus*.

Advantageously, the extract of *Astragalus membranaceus* is prepared from two extracts of *Astragalus membranaceus* roots, a first extract which is hydroalcoholic, and a second extract which is aqueous.

Typically, the extraction solvent for the first extract is a water-ethanol mixture. Preferably, the water-ethanol mixture comprises at least 50% by volume, preferably at least 75% by volume, for example such as 85% by volume ethanol.

Advantageously, the weight ratio of water-ethanol to powder of *Astragalus membranaceus* roots is between 200:1 and 50:1, preferably between 150:1 and 100:1, such as of the order of 125:1.

The extraction of the second extract is carried out by a solvent consisting of water.

Typically, the weight ratio of water to powder of *Astragalus membranaceus* roots is comprised between 10:1 and 2:1, preferably between 7:1 and 3:1, such as of the order of 5:1.

The extraction of *Astragalus* can also be carried out according to the usual methods (percolation, infusion, decoction, maceration) well known to the person skilled in the art. Preferably, the extraction of the powder is repeated several times. Advantageously, the extraction is carried out hot, preferably at a moderate temperature (40 to 100° C.). After extraction, the extract is preferably dried.

According to a particular embodiment of the invention, the product containing an extract of *Rhodiola* and an extract of *Astragalus* as combined products further comprises an ingredient selected from the group consisting of tocopherol, selenium, silicon, zinc, magnesium, polyphenols other than those derived from *Rhodiola* and *Astragalus* extracts, or mixtures thereof.

Preferably, the tocopherol is introduced into the product in an amount comprised between 0.05% and 2% by weight with respect to the total weight of product.

Preferably, the selenium is introduced into the product in an amount comprised between 0.0001% and 0.005% by weight with respect to the total weight of product, for example in the form of selenium yeast.

Preferably, the silicon is introduced into the product in an amount comprised between 6% and 10% by weight with respect to the total weight of product, for example in the form of natural (uncalcined) diatoms, silicon dioxide, silicate(s) and/or orthosilicic acid (generic names: organic silicon, biogenic silicon).

Preferably the zinc is introduced into the product in an amount comprised between 0.01% and 0.5% by weight with respect to the total weight of product, for example in the form of zinc salt(s), such as zinc citrate, sulfate and/or bisglycinate.

The magnesium is preferably introduced into the product in an amount comprised between 5% and 50% by weight with respect to the total weight of product, for example in the form of magnesium salt(s) such as magnesium glycerophosphate and/or magnesium citrate.

The polyphenols may be present in the product through the introduction of a plant extract, such as an extract of *Vitis vinifera* (common grape vine) and/or of *Polygonum cuspidatum* (Japanese knotweed). Preferably, the polyphenols are introduced into the product in an amount comprised between 1% and 10% by weight with respect to the total weight of product.

Preferably, one polyphenol is resveratrol (natural or synthetic). Advantageously, the resveratrol is introduced into the product in an amount comprised between 0.1% and 3% by weight with respect to the total weight of product.

In a preferred embodiment of the invention, the product containing an extract of *Rhodiola* and an extract of *Astragalus* as combined products comprises all of the above ingredients.

In this preferred embodiment, the product containing an extract of *Rhodiola* and an extract of *Astragalus* as combined products may then comprise at least 3.5% by weight of a *Rhodiola* extract, preferably at least 4% by weight, more preferably at least 4.5% by weight of a *Rhodiola* extract, with respect to the total weight of product.

It may also comprise at least 3.5% by weight of an extract of *Astragalus*, preferably at least 4% by weight, more preferably at least 4.5% by weight of an extract of *Astragalus* with respect to the total weight of product.

Preferably, the extracts are dry extracts.

Advantageously, the extracts of *Rhodiola* and of *Astragalus* are as described above.

According to a particularly preferred embodiment, the product according to the invention contains:

an extract of *Rhodiola rosea* comprising at least 1.5% by weight of rosavin and at least 0.25% by weight of salidroside, preferably at least 2% by weight of rosavin and at least 0.5% by weight of salidroside, more preferably, at least 2.5% by weight of rosavin and at least 0.75% by weight of salidroside, still more preferably at least 3% by weight of rosavin and at least 1% by weight of salidroside, with respect to the total weight of dry extract of *Rhodiola rosea*, and an extract of *Astragalus membranaceus* comprising at least 0.2% by weight of astragalosides and at least 10% by weight of polysaccharides, preferably, at least 0.4% by weight of astragalosides and at least 12% by weight of polysaccharides, more preferably, at least 0.6% by weight of astragalosides and at least 14% by weight of polysaccharides, still more preferably at least 0.8% by weight of astragalosides and at least 16% by weight of polysaccharides, based on the total weight of dry extract of *Astragalus membranaceus*.

Advantageously, according to this particularly preferred embodiment, the product containing the extracts of *Rhodiola rosea* and of *Astragalus membranaceus*, as well as said extracts, are as described above, including the embodiments and in particular the ratios, doses and percentages by weight described above.

The invention also relates to a method of treating a neurodegenerative disease comprising administering an extract of *Rhodiola* and an extract of *Astragalus* simultaneously, separately or spread over time. It also concerns a method of preventing a neurodegenerative disease comprising administering an extract of *Rhodiola* and an extract of *Astragalus* simultaneously, separately or spread over time.

Advantageously, the extract of *Rhodiola* and the extract of *Astragalus* form a product such as a combined product, administrable to the patient in the form of capsule(s), pill(s) and/or tablet(s).

The particular, advantageous and preferred features of the methods according to the invention are as described above, in particular as regards the extracts, the product and the doses.

Other features and advantages of the invention will appear in the following examples, given by way of illustration, with reference to the Figures:

FIG. 1 presents four diagrams illustrating the cytotoxicity results of the extract of *Rhodiola*, of *Astragalus*, of the combination of extracts ("Mix") and the product "ADN-Téloméractives", after 48 hours of exposure. The results are expressed in a mean standard deviation +/− of 3 replicates;

FIG. 2 presents four diagrams illustrating the curative effect of extract of *Rhodiola*, of *Astragalus*, of the combination of extracts and of the product "ADN-Téloméractives" on the length of neurites after 48 hours in the Alzheimer model. The results are expressed in a mean standard deviation +/− of 3 replicates;

FIG. 3 comprises three photographs illustrating the effect of 250 µg/mL of *Rhodiola* on differentiated SH-SY5Y (cells) exposed in advance to 10 µM of Aftin-5 for 48 hours. 20× magnification, nuclei in blue, tubulin B3 in green;

FIG. 4 comprises three photographs illustrating the effect of 250 µg/mL of *Astragalus* on differentiated SH-SY5Y (cells) exposed in advance to 10 µM of Aftin-5 for 48 hours. 20× magnification, nuclei in blue, tubulin B3 in green;

FIG. 5 comprises three photographs illustrating the effect of 250 µg/mL of the combination of extracts of *Rhodiola* and *Astragalus* on differentiated SH-SY5Y (cells) exposed in advance to 10 µM of Aftin-5 for 48 hours. 20× magnification, nuclei in blue, tubulin B3 in green;

FIG. 6 comprises three photographs illustrating the effect of 25.00 µg/mL of "ADN-Téloméractives" product on differentiated SH-SY5Y (cells) exposed in advance to 10 µM of Aftin-5 for 48 hours. 20× magnification, nuclei in blue, tubulin B3 in green;

Figure 10:
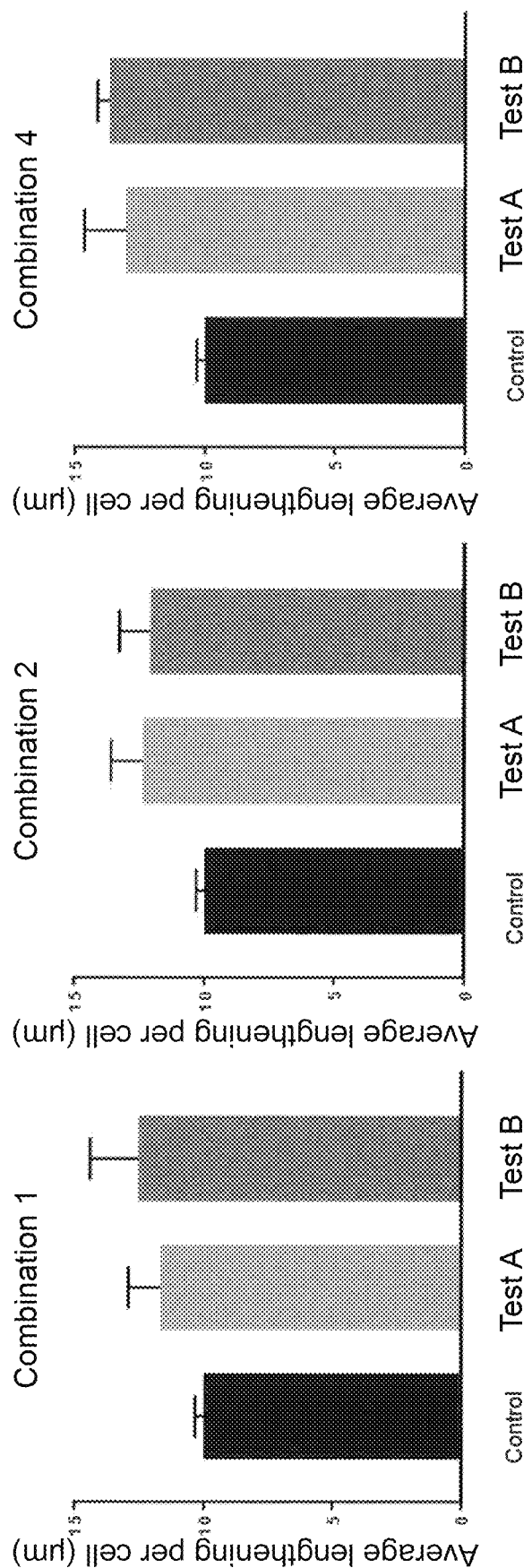
Figure 11:
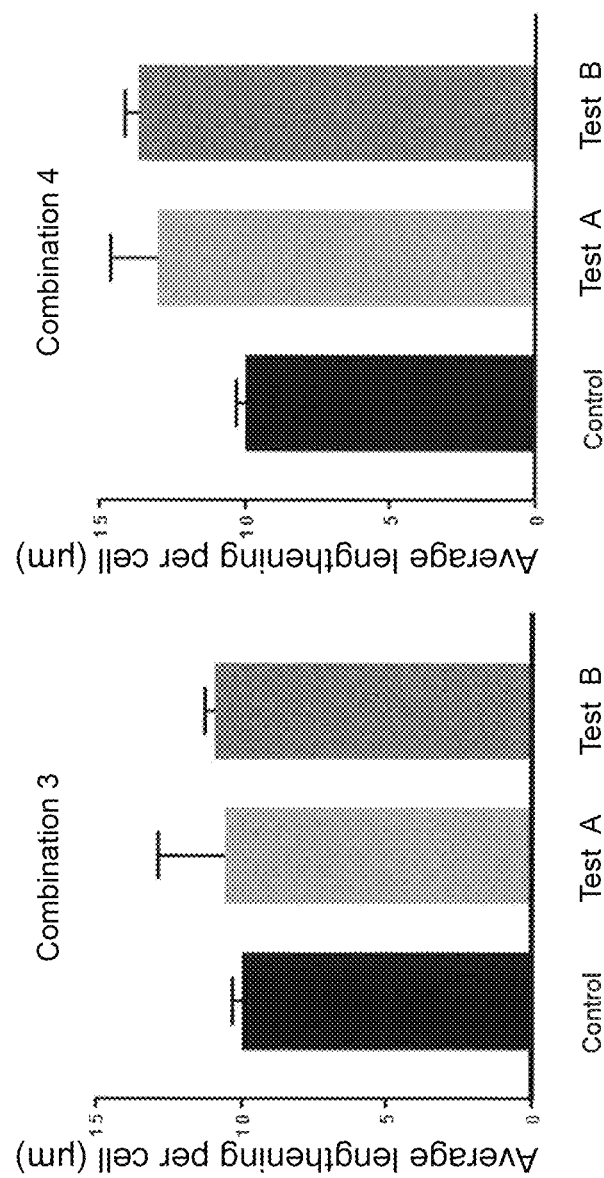

FIG. 10 presents three diagrams illustrating the effect of a combination of extracts of *Rhodiola* and *Astragalus* not including astragalosides (Combination 1), of a combination of extracts of *Rhodiola* and *Astragalus* not including polysaccharides (Combination 2) and of the combination of extracts of *Rhodiola* and *Astragalus* described in Example 1 (Combination 4) on the length of neurites after 48 hours in the Alzheimer's model; and FIG. 11 shows two diagrams illustrating the effect of a combination of *Rhodiola* and *Astragalus* extracts not including rosavin (Combination 3) and of the combination of extracts of *Rhodiola* and *Astragalus* described in Example 1 (Combination 4) on neurite length after 48 hours in the Alzheimer's model.

Example 1: Preparation of Products for Use According to the Invention

1. Materials and Methods
1.1 Products
The following products were used:
A *Rhodiola* extract obtained by hydroalcoholic extraction from ground roots of *Rhodiola rosea*, the extraction solvent consisting of 70% by volume of water and 30% by volume of ethanol, in a weight ratio of solvent to root powder of the order of 8:1. This extract of *Rhodiola* comprises at least 3% by weight of rosavin and at least 1% by weight of salidroside, with respect to the total weight of dry extract of *Rhodiola*;

A first extract of *Astragalus* obtained by hydroalcoholic extraction from ground roots of *Astragalus membranaceus*, the extraction solvent consisting of 15% by volume of water and 85% by volume of ethanol, in a weight ratio of solvent to root powder of the order of 125:1;

A second *Astragalus* extract obtained by extraction with pure water from ground roots of *Astragalus membranaceus*, in a weight ratio of water to root powder of the order of 5:1;

The "ADN-Téloméractives" product marketed by HBN, comprising the combination of an extract of *Rhodiola* and of an extract of *Astragalus*. The product also contains tocopherol, selenium in the form of yeasts, silicon, particularly in the form of marine diatoms, zinc, magnesium, an extract of *Vitis vinifera* as well as an extract of *Polygonum cuspidatum* containing 25% resveratrol. The product also contains various vitamins.

Preparation of the Combined Extract of *Astragalus*:

The two above-mentioned *Astragalus* extracts are mixed so as to obtain a combined *Astragalus* extract comprising at least 16% by weight of polysaccharides and at least 0.8% by weight of a mixture of astragalosides I, II, III, IV, V, VI and VII, based on the total weight of dry extract of *Astragalus*.

Preparation of the Combination of Extracts of *Rhodiola* and of *Astragalus*:

The combination of an extract of *Rhodiola* and of an extract of *Astragalus* for use according to the invention is prepared by mixing the above-mentioned extract of *Rhodiola* with the combined extract of *Astragalus* in a weight ratio of 1:1.

Aqueous solutions of extract of *Rhodiola*, of the combined extract of *Astragalus*, of the combination of extracts and of the product "ADN-Téloméractives" were freshly prepared with a range of 8 final concentrations (0.00125-0.0025-0.0050-0.0125-0.025-0.05-0.125-0.25 mg/mL).

1.2 Cell Culture and Differentiation
SH-SY5Y (ATCC, CRL-2266) cells were cultured and transplanted according to the supplier's recommendations.

All tests were performed in three technical replicates using 96-well microplates. After inoculation, SH-SY5Y cells were differentiated by exposure to retinoic acid (10 µM) for 4 days.

1.3 Cell Fixation and Staining

After each test, the cells were fixed using a mixture of methanol and acetone at room temperature for 5 minutes, before staining the nuclei with Hoechst and immunostaining the B3 tubulin (secondary antibody conjugated to an Alexa 488 fluorochrome).

1.4 Cytotoxicity

Cytotoxicity was evaluated using staining and counting of cell nuclei (cell counts were evaluated using MetaXpress (Molecular Devices)).

1.5 Statistical Analysis

Statistical comparison of the results to the control conditions was performed using a t-test. The significance was expressed with the symbol "*" when $p<0.05$.

2. Results on the Cytotoxicity of *Astragalus*, *Rhodiola*, the Combination of Extracts and the Product "ADN-Téloméractives" (ADN-T)

Figure 1:
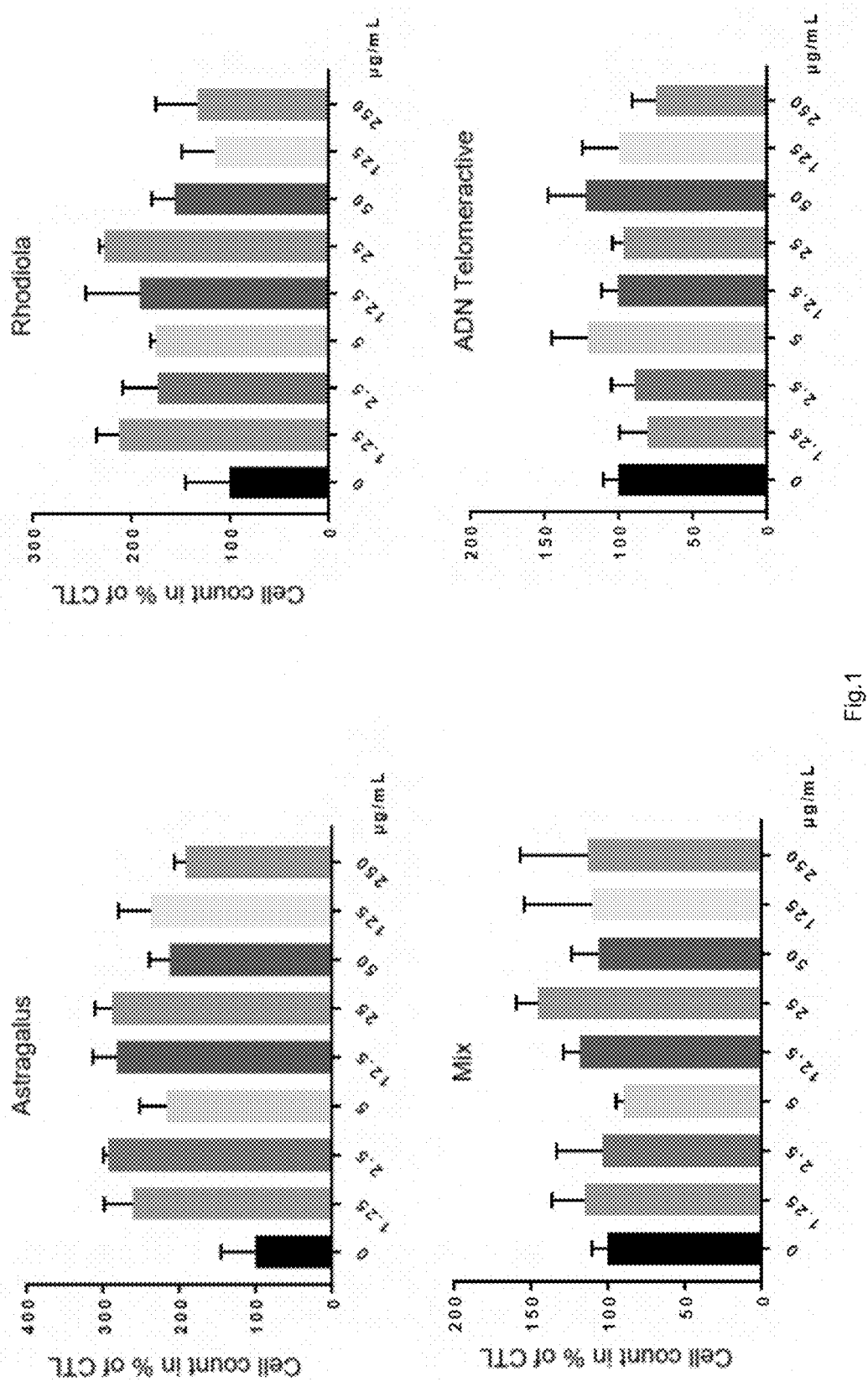

Cytotoxicity was evaluated on differentiated SH-SY5Y (cells) after 48 hours of exposure to *Astragalus* extract, to extract of *Rhodiola*, to the combination of extracts and to the product "ADN-Téloméractives". None of the products showed a cytotoxic effect (see FIG. 1). *Astragalus* and *Rhodiola* induced an increase in viability compared to the control. The viability of SHSY-5Y (cells) exposed to the combination of extracts and the product "ADN-Téloméractives" is close to the viability of the control, regardless of the doses tested.

Example 2: Synergistic Effect of an Extract of *Rhodiola* and of an Extract of *Astragalus* for Use According to the Invention 1. Materials and Methods The products, cell culture and differentiation, cell fixation and staining, cytotoxicity and statistical analysis are as shown in Example 1.

1.1 Curative Test

Models of neurodegenerative diseases can be established in the laboratory using differentiated neuronal cell lines. Using chemical inducers (Aftin-5, in this case), a model of Alzheimer's disease can be obtained with the human neuroblastoma cell line SH-SY5Y. The neuroprotective and curative properties of the combination of extracts are evaluated following neurotoxic aggression by counting neurons and measuring the length of neurites.

The cells were exposed for 2 days with 10 µM of Aftin-5 alone. They were then treated for 48 hours with aqueous dilutions of *Rhodiola*, of *Astragalus*, of a combination of extracts, of "ADN-Téloméractives" product or simply water (control), in co-incubation with Aftin-5 (10 µM). After fixation and labeling, neurite outgrowth and cell counts were evaluated using MetaXpress (Molecular Devices).

1.2 Cellular Imaging and Image Analysis

The images were obtained using an ImageXpress® Micro XLS (Molecular Devices) automated microscope with a 20× objective. Two dichroic filters were used simultaneously to specifically detect the different probes used. Four fields per well were recorded and analyzed individually.

The images were analyzed using MetaXpress (Molecular Devices) software.

2. Results: Curative Effect

Figure 2:
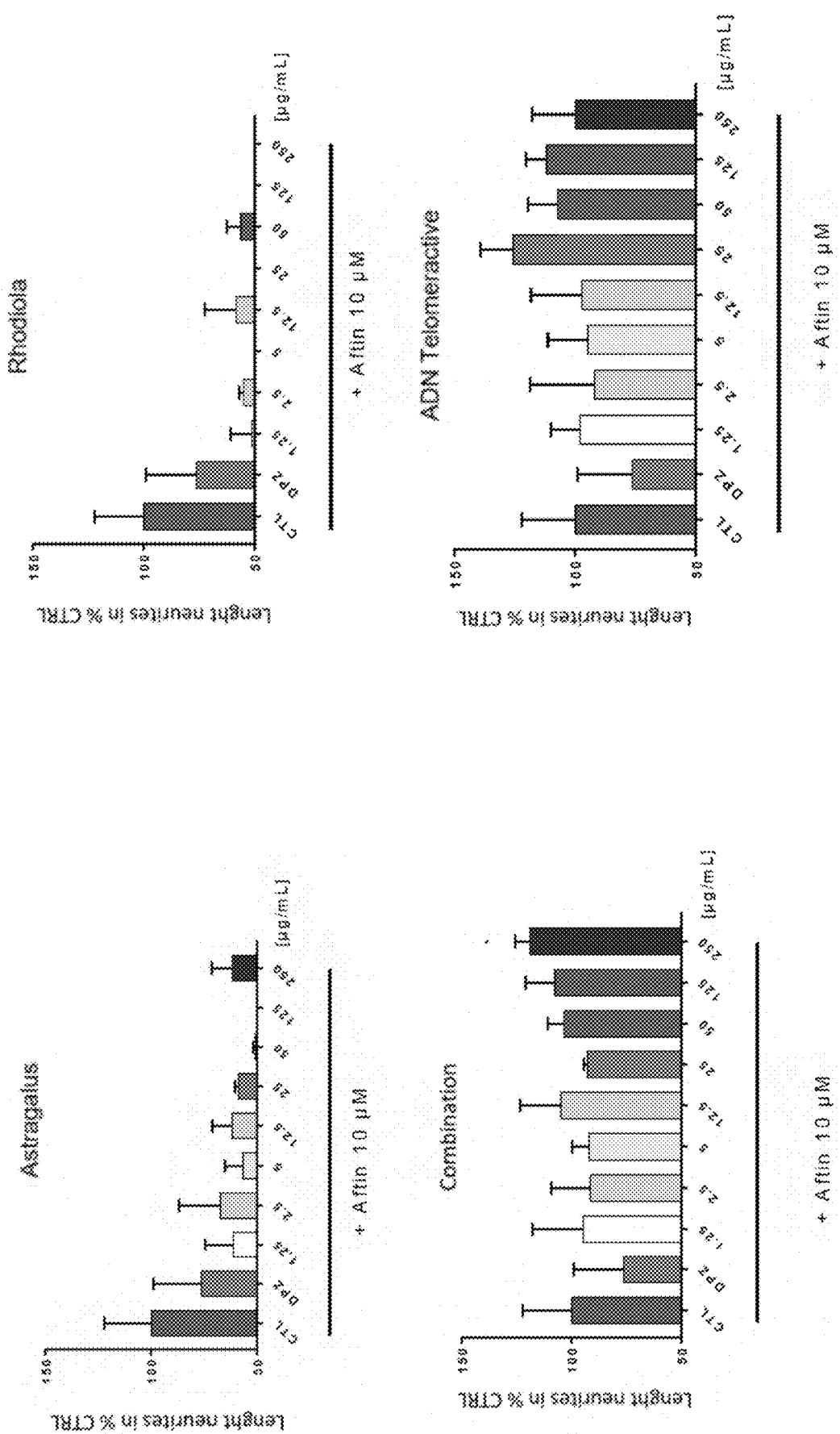

The results are presented in FIG. 2.

In this Figure, it may be observed that the *Rhodiola* and the *Astragalus* did not cure the neurodegenerative phenotype induced by 48 hours exposure to 10 µM d'Aftin-5. On the contrary, at all the tested doses, a length of neurites less than that presented by the control was observed.

By contrast, it can be observed that the combination of extracts of *Rhodiola* and of *Astragalus* showed a dose-dependent increased curative effect against the induced Alzheimer's phenotype. The effect of the dose increased from 12.50 µg/mL to 250 µg/mL. At 250 µg/mL, the curative effect was significantly different from the control with a 119.1% increase in neurite length. A U-shaped dose effect was also observed with the product "ADN-Téloméractives" with a peak at 25.00 µg/mL for a neurite length at 125.9. This value was not significantly different from the control, but compared to the whole cell population, a statistical difference is shown by the t-test.

It follows that *Rhodiola* alone and *Astragalus* alone do not enable the length of the neurites to be improved: on the contrary, it is deteriorated relative to the control.

By contrast the combination of the extracts of *Rhodiola* and of *Astragalus* extracts enables, surprisingly, a maintenance and even an extension of the length of the neurites.

It follows that the combination of extracts has a synergistic curative effect in a model of neurodegenerative diseases and more specifically, a model of Alzheimer's disease.

Figure 3:
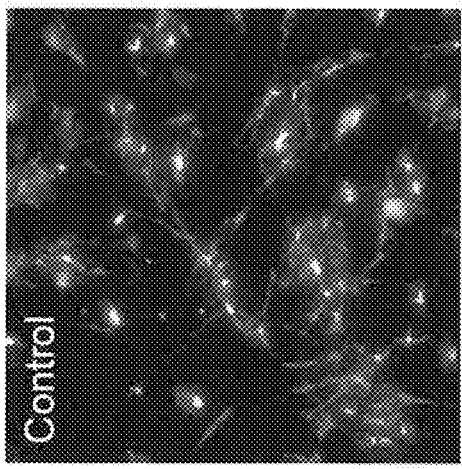
Figure 3:
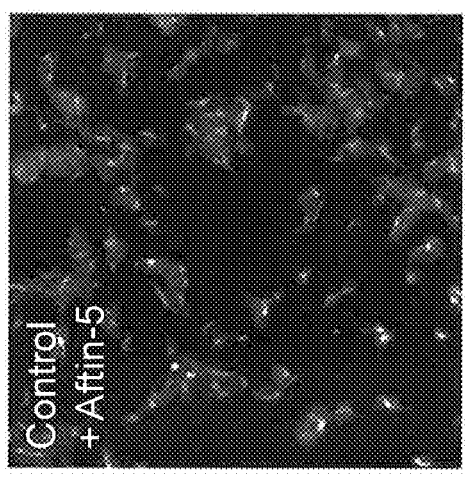
Figure 3:
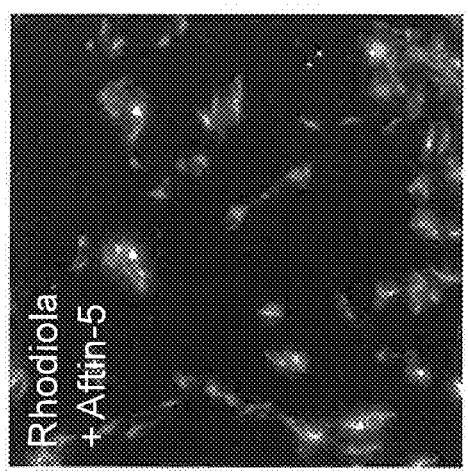

FIG. 3 shows three photographs illustrating the effect of 250 µg/mL of *Rhodiola* on differentiated SH-SY5Y (cells) exposed in advance to 10 µM of Aftin-5 for 48 hours. It can be observed from this Figure that, compared to the control, cells exposed to Aftin-5 show a significant reduction in neurite length. The cells co-exposed to Aftin-5 and *Rhodiola* show a shorter neurite length than those exposed to Aftin-5 alone.

Figure 4:
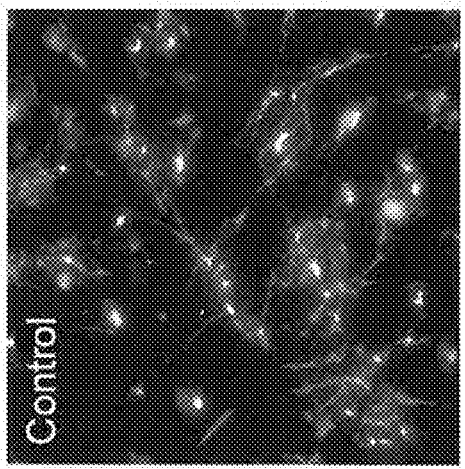
Figure 4:
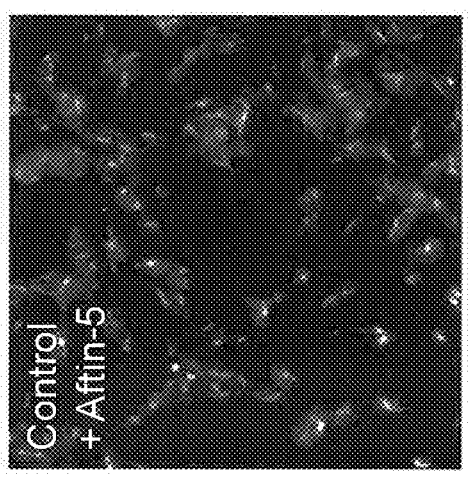
Figure 4:
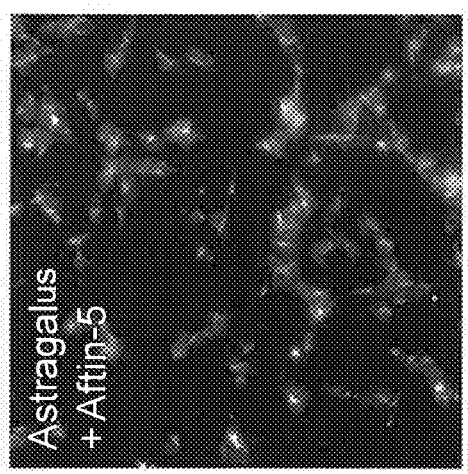

FIG. 4 shows three photographs illustrating the effect of 250 µg/mL of *Astragalus* on differentiated SH-SY5Y (cells) exposed in advance to 10 µM of Aftin-5 for 48 hours. As in the previous Figure, it can be observed in this Figure that, compared to the control, the cells exposed to Aftin-5 show a significant reduction in neurite length. The cells co-exposed to Aftin-5 and *Astragalus* show a shorter neurite length than those exposed to Aftin-5 alone.

Figure 5:
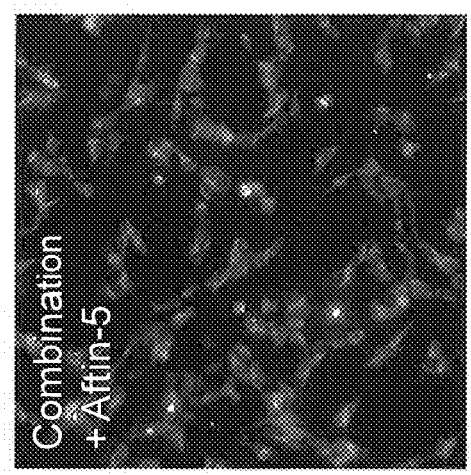
Figure 5:
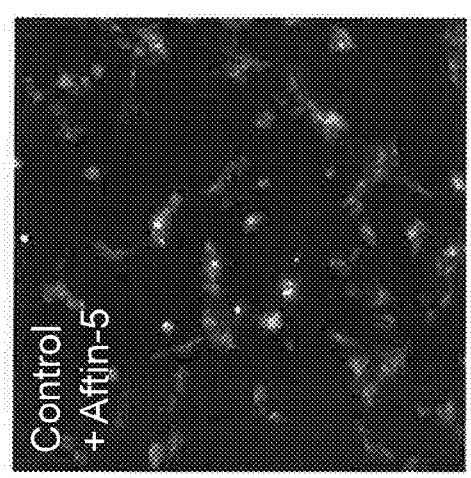
Figure 5:
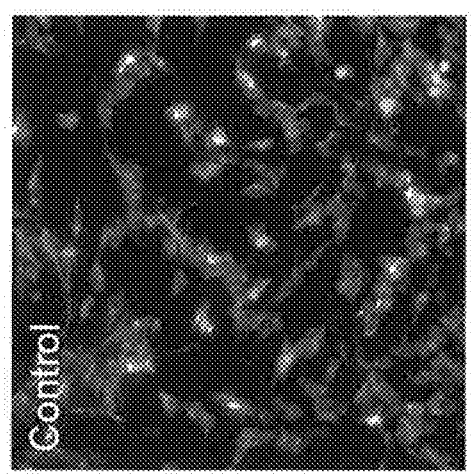

FIG. 5 comprises three photographs illustrating the effect of 250 µg/mL of the combination of extracts of *Rhodiola* and of *Astragalus* on differentiated SH-SY5Y (cells) exposed in advance to 10 µM of Aftin-5 for 48 hours. As in the previous Figures, it is observed in this Figure that, compared to the control, the cells exposed to Aftin-5 show a significant reduction in length of the neurites. The cells co-exposed to Aftin-5 and to 250 µg/mL of the combination of extracts of *Rhodiola* and of *Astragalus* show better viability and greater neurite length than those exposed to Aftin-5 alone.

Figure 6:
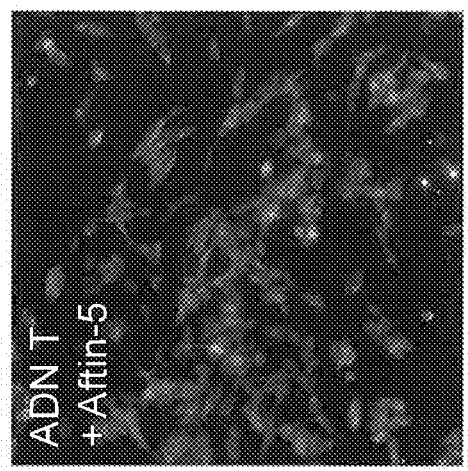
Figure 6:
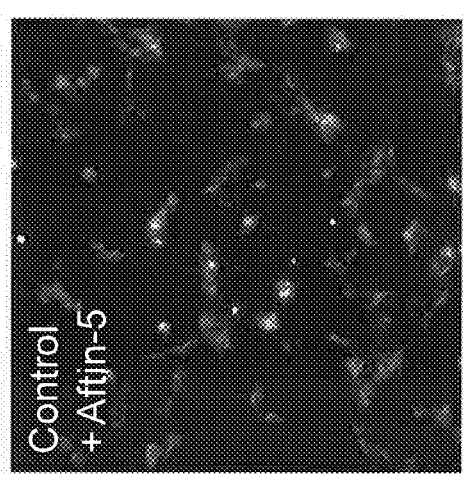
Figure 6:
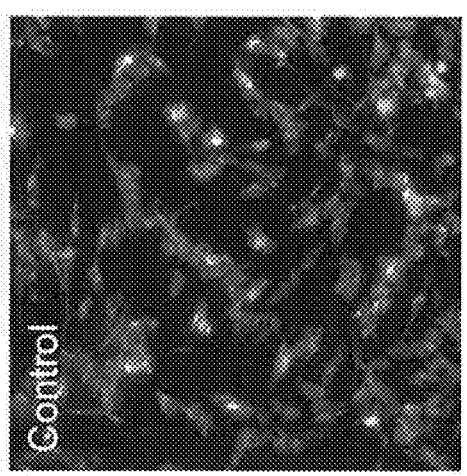

FIG. 6 comprises three photographs illustrating the effect of 25.00 µg/mL of "ADN-Téloméractives" product on differentiated SH-SY5Y (cells) exposed in advance to 10 µM of Aftin-5 for 48 hours. As in the previous Figures, it is observed in this Figure that, compared to the control, the cells exposed to Aftin-5 show a significant reduction in length of the neurites. The cells co-exposed to Aftin-5 and to 25.00 µg/mL of "ADN-Téloméractives" product show better viability and greater length of neurites than those exposed to Aftin-5 alone.

Example 3: Neuroprotective Effect of an Extract of *Rhodiola* and of an Extract of *Astragalus* for Use According to the Invention 1. Materials and Methods The products, cell culture and differentiation, cell fixation and staining, cytotoxicity and statistical analysis are as shown in Example 1.

1.1 Neuroprotection Test

The cells were exposed for 48 hours to aqueous dilutions of *Rhodiola, Astragalus*, a combination of extracts and the product "ADN-Téloméractives", with 30 µM of Aftin-5 (a phenotypic inducer of Alzheimer's disease). After fixation and labeling, neurite outgrowth and cell counts were evaluated using MetaXpress (Molecular Devices).

2. Results: Neuroprotective Effect

*Rhodiola, Astragalus*, the extract combination and the product "ADN-Téloméractives" showed a significant protective effect against the phenotype of Alzheimer's disease induced by Aftin-5 (30 µM). Both the *Astragalus* and the *Rhodiola* showed a neuroprotective effect at 1.25 and 2.50 µg/mL, increasing the length of neurites to 129.9 and 127.9 respectively. The mixture of extracts of *Astragalus* and of *Rhodiola* induced a neuroprotective effect at 1.25 µg/mL, with an increase in neurite length of 125.6% compared to the control. The product "ADN-Téloméractives" induced a neuroprotective effect at 2.50 µg/mL, the length of the neurites being 126.8% compared to the control.

Example 4: Effect of the Product "ADN-Téloméractives" on DNA Repair Systems

1. Materials and Methods 1.1 Solubilization of the Product "ADN-Téloméractives" (ADN-T)

After milling "ADN-Téloméractives" product, an aqueous stock solution is prepared at 12.5 mg/mL. It is stirred at 37° C. for 1 hour. The residues are then removed by centrifugation at 1500 rpm for 5 minutes.

1.2 Model

The model consists in studying the involvement of the DNA repair systems in the protective effect of the product "ADN-Téloméractives" against genotoxins, using an in vitro approach on HepG2 cells, brought into contact with the genotoxic agent EMS (ethyl methane sulfonate).

1.3 Experimental Design

1. Pretreatment of cells with the solution of "ADN-Téloméractives" product.

Day 0: at 9:00 a.m., inoculation of the wells with the cells, then at 3:00 p.m., addition of "ADN-Téloméractives" product at 40 µg/mL.

2. Introduction of the Genotoxic Compound EMS

Day 2: at 3:00 p.m. introduction of the EMS at two concentrations: 0.2 mM and 1 mM.

3. Putting the cells back in the presence of the "ADN-Téloméractives" product.

Day 3: at 8:00 a.m., addition of "ADN-Téloméractives" at 40 µg/mL.

4. Harvesting and analysis

Day 4: at 8:00 a.m., harvesting

A control without "ADN-Téloméractives" product is conducted in parallel.

TABLE 1

Lists of the conditions tested

| ADN-T pre-treatment (µg/mL) | Genotoxic treatment (mM) | ADN-T post-treatment (µg/mL) |
|---|---|---|
| 0 | 0 | 0 |
| 0 | 0.2 | 0 |
| 0 | 1 | 0 |
| 40 | 0 | 40 |
| 40 | 0.2 | 40 |
| 40 | 1 | 40 |

1.4 Analyses

The extracts are deposited on a chip functionalized by plasmids comprising series of specific DNA lesions:

8oxoG (8oxoG)

ethenobases (Etheno)

Glycols of thymine and cytosine (Glycols)

abasic sites (AbaS)

photoproducts (pyrimidine dimers and 6-4 photoproducts) (CPD-64)

The DNA repair enzymes, contained in the extracts, excise the lesions (or the DNA fragment surrounding the lesions) and incorporate a fluorescent marker (dCTP-Cy3) during DNA resynthesis.

The fluorescent signal is quantified using a scanner. It is proportional to the Excision/Resynthesis capacities of each extract with respect to each lesion.

This test is used to characterize the Basic Excision Repair (BER) and Nucleotide Excision Repair (NER) systems.

The extract concentration is 0.2 mg/mL.

Each sample is tested on 2 chips. Each chip has 4 spots per lesion. The results are then normalized (NormalizeIt).

The value of the Control plasmid (no lesion) is subtracted from the total intensity value obtained for each lesion.

The results are given in Total Fluorescence Intensity for each lesion+/−Standard Deviation.

2. Results

Figure 7:
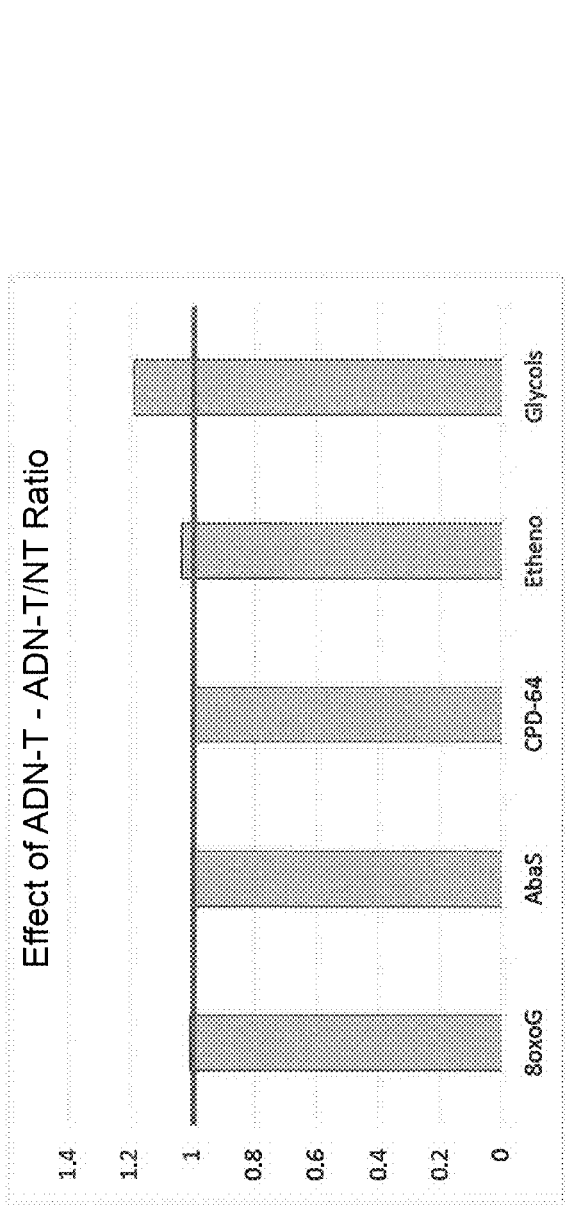
FIG. 7 is a diagram illustrating the effect of the product "ADN-Téloméractives" on the repair of DNA lesions (8oxoG, Etheno, Glycols, AbaS, CPD-64) in HepG2 cells.
Figure 8:
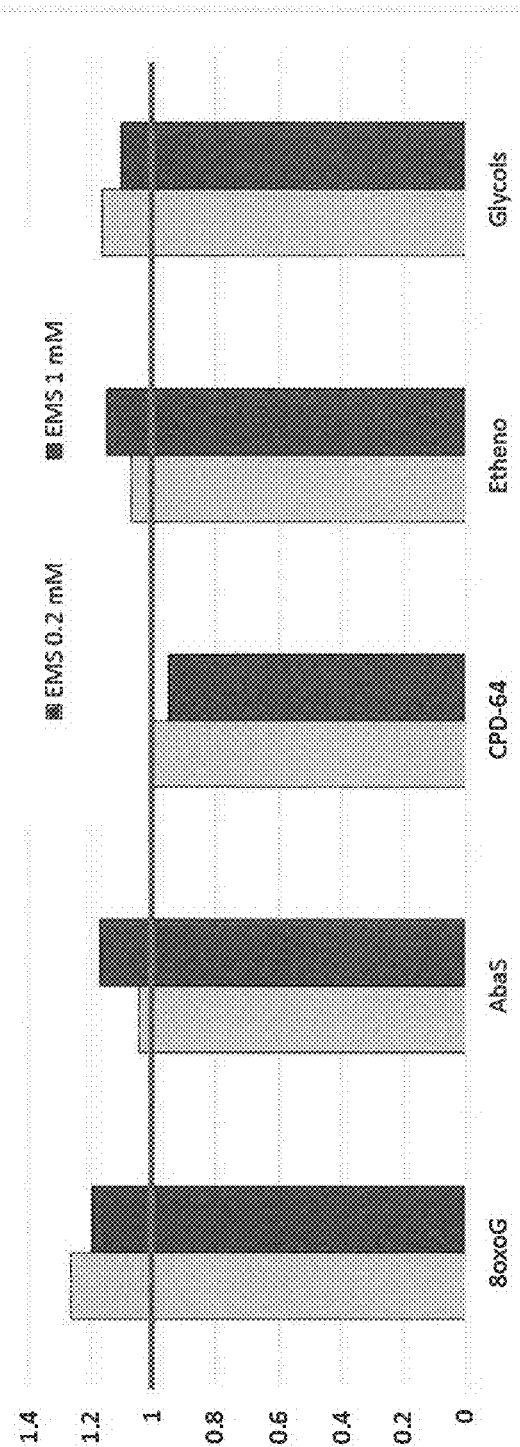
FIG. 8 is a diagram illustrating the effect of the genotoxic EMS on the repair of DNA lesions (8oxoG, Etheno, Glycols, AbaS, CPD-64) in HepG2 cells.
Figure 9:
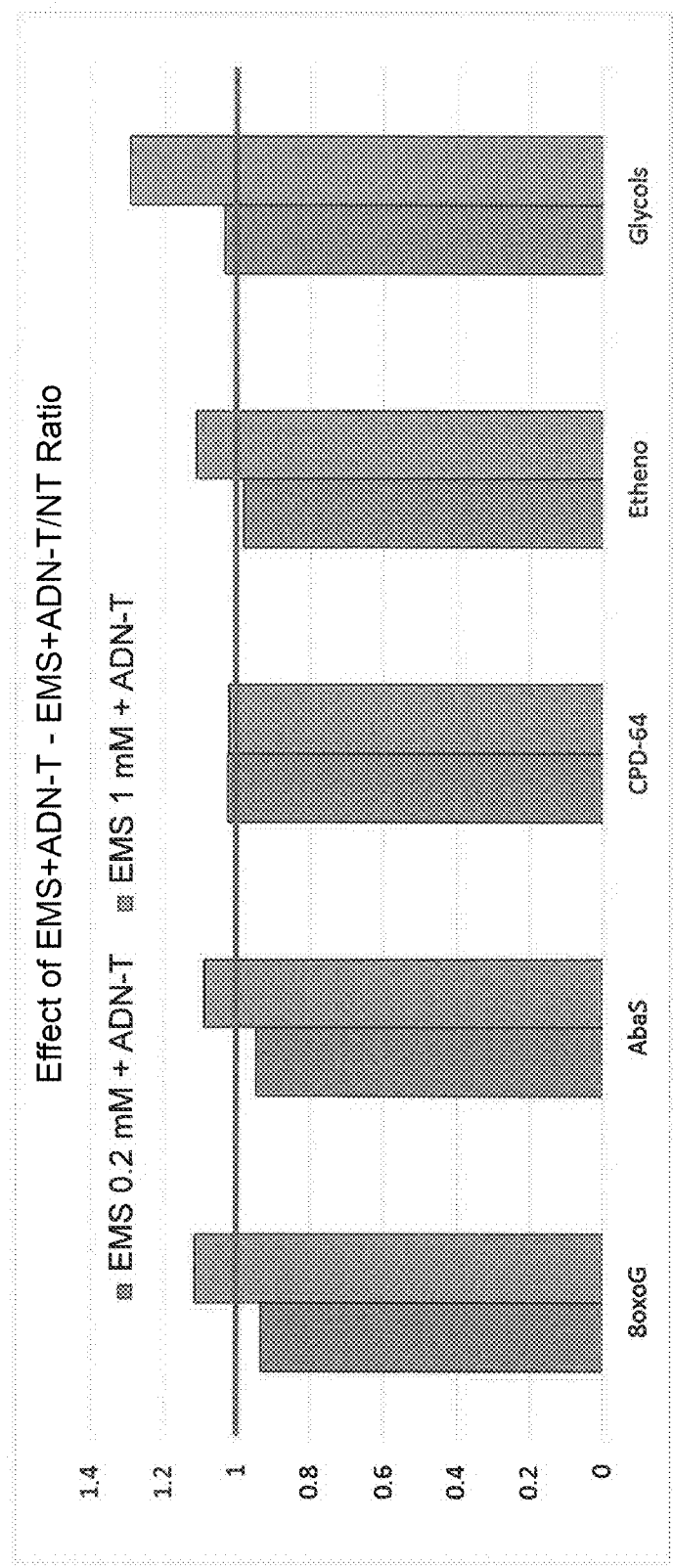
FIG. 9 is a diagram illustrating the effect of pre-treatment and post-treatment with the product "ADN-Téloméractives" on repair of EMS-induced DNA lesions (8oxoG, Etheno, Glycols, AbaS, CPD-64) in HepG2 cells.

The results are presented in FIGS. 7, 8 and 9.

In FIG. 7, it is observed that at the non-cytotoxic dose tested, the product "ADN-Téloméractives" had no effect on the DNA repair systems, except for a clear repair simulating effect on glycols.

In FIG. 8, it is observed that at least at the highest concentration tested, EMS exclusively stimulates Basic Excision Repair (BER). The repair of photoproducts (CPD-64) managed by Nucleotide Excision Repair (NER) is not affected. This result is in favor of the formation by EMS of small alkylation or oxidation-type lesions, which would induce the activation of the enzymes managing them.

This result conforms to what is expected.

Lastly, in FIG. 9, it is observed that the pre-treatment of the cells with the product "ADN-Téloméractives" completely cancels the impact of EMS used at the lowest concentration, on the DNA repair systems.

Still, induction of the DNA repair systems at the highest concentration of EMS persists. This induction is however lower than with EMS alone, except for glycol lesion. Stimulation of repair of the Glycols lesion evokes the effect of the product "ADN-Téloméractives".

Thus:

The "ADN-Téloméractives" product alone, at a non-cytotoxic dose, has a significant action of stimulating glycol repair.

Pretreatment with the product "ADN-Téloméractives" cancels the effects of the lowest dose of EMS and reduces the effects of the highest dose.

At the lowest dose of EMS, the "ADN-Téloméractives" product, in sufficient quantity, inactivates EMS with respect to its genotoxic effects on DNA.

At the highest dose of EMS, the "ADN-Téloméractives" product, probably in a limiting quantity, would not be sufficient to inactivate all of the EMS present, but would reduce its impact.

Example 5: Effect of Certain Active Ingredients of an Extract of *Rhodiola* and of an Extract of *Astragalus* for Use According to the Invention 1. Materials and methods 1.1 Products The following products were used:

The first extract of *Astragalus* as described in Example 1 (obtained by hydroalcoholic extraction from ground roots of *Astragalus membranaceus*). This extract comprises at least 4% by weight of a mixture of astragalosides I, II, III, IV, V, VI and VII, with respect to the total weight of dry extract of *Astragalus*, but does not comprise polysaccharides;

The second extract of *Astragalus* as described in Example 1 (obtained by extraction with pure water from ground roots of *Astragalus membranaceus*). This extract comprises at least 20% by weight of polysaccharides, with respect to the total weight of dry extract of *Astragalus*, but does not contain astragalosides;

The *Rhodiola* extract as described in Example 1 (*Rhodiola* Extract 1), comprising at least 3% by weight of rosavin and at least 1% by weight of salidroside, with respect to the total weight of dry extract of *Rhodiola*;

A *Rhodiola* extract comprising at least 3% by weight of salidroside (*Rhodiola* Extract 2), with respect to the total weight of dry extract of *Rhodiola*, but not comprising rosavin (supplied by Gonmisol);

The combination of extracts of *Rhodiola* and of *Astragalus* described in Example 1, hereinafter referred to as combination 4, the extract of *Rhodiola* comprising at least 3% by weight of rosavin and at least 1% by weight of salidroside, with respect to the total weight of dry extract of *Rhodiola*, and the extract of *Astragalus* comprising at least 16% by weight of polysaccharides and at least 0.8% by weight of a mixture of astragalosides I, II, III, IV, V, VI and VII, with respect to the total weight of dry extract of *Astragalus*.

Preparation of Combinations of Extracts

In addition to combination 4, the preparation of which is described in Example 1, three other combinations of extracts are prepared:

Combination 1: This combination is prepared by mixing the second extract of *Astragalus* (not comprising astragalosides) and *Rhodiola* extract 1 in a weight ratio of 4:5;

Combination 2: This combination is prepared by mixing the first extract of *Astragalus* (comprising no polysaccharides) and *Rhodiola* extract 1 in a weight ratio of 1:5;

Combination 3: This combination is prepared by mixing the first *Astragalus* extract, the second *Astragalus* extract and the above-mentioned *Rhodiola* extract 2 not comprising rosavin in a weight ratio of 3:12:5.

Preparation of Aqueous Solutions from Combinations of Extracts

For each combination, two aqueous solutions were freshly prepared to compare the effects of astragalosides, polysaccharides and rosavin, the concentrations being given in Tables 2 and 3 below.

TABLE 2

Concentrations of the aqueous solutions tested for Test A

| Combination | Concentration combination (mg/mL) | Rosavin (mg/mL) | Salidroside (mg/mL) | Polysaccharides (mg/mL) | Astragalosides (mg/mL) |
|---|---|---|---|---|---|
| 1 | 0.0225 | 0.0003750 | 0.0001250 | 0.0020000 | — |
| 2 | 0.0150 | 0.0003750 | 0.0001250 | — | 0.0001000 |
| 3 | 0.0167 | — | 0.0001250 | 0.0020000 | 0.0001000 |
| 4 | 0.0250 | 0.0003750 | 0.0001250 | 0.0020000 | 0.0001000 |

TABLE 3

Concentrations of the aqueous solutions tested for Test B

| Combination | Concentration combination (mg/mL) | Rosavin (mg/mL) | Salidroside (mg/mL) | Polysaccharides (mg/mL) | Astragalosides (mg/mL) |
|---|---|---|---|---|---|
| 1 | 0.0450 | 0.0007500 | 0.0002500 | 0.0040000 | — |
| 2 | 0.0300 | 0.0007500 | 0.0002500 | — | 0.0002000 |
| 3 | 0.0333 | — | 0.0002500 | 0.0040000 | 0.0002000 |
| 4 | 0.0500 | 0.0007500 | 0.0002500 | 0.0040000 | 0.0002000 |

1.2 Cell Culture and Differentiation

SH-SY5Y cells were cultured and transplanted according to the supplier's recommendations.

All tests were performed in three technical replicates using 96-well microplates. After inoculation, the SH-SY5Y cells were differentiated by exposure to staurosporin (25 nM in 1% fetal calf serum complete culture medium) for 3 days.

1.3 Cell Fixation and Staining

After each test, the cells were fixed using a mixture of formaldehyde and methanol (marketed by Sigma-Aldrich under the name "Formalin 10%") at room temperature for 10 minutes, followed by permeabilization in 0.5% Tween 20 (P2287 marketed by Sigma-Aldrich) for 30 minutes and finally staining the nuclei with Hoechst and indirect immunocytochemical labeling of ß3 tubulin to distinguish neurites (rabbit anti ß3 tubulin antibody (ab18207 marketed by Abcam) and rabbit anti-IgG secondary antibody conjugated to Alexa 488 fluorochrome (marketed by Ozyme)) for 1 hour.

1.4 Curative Test

The cells were exposed for 2 days with 10 µM Aftin-5 alone. They were then treated for 48 hours with the aqueous solutions given in Table 2 or simply with water (control), co-incubating with Aftin-5 (10 µM). After fixation and labeling, neurite outgrowth was evaluated using MetaXpress (Molecular Devices).

1.5 Cellular Imaging and Image Analysis

The images were obtained using an ImageXpress® Micro Confocal System (Molecular Devices) automated microscope with a 20× objective. Two dichroic filters were used simultaneously to specifically detect the different probes used. Four images per well were recorded and analyzed individually.

The images were analyzed using MetaXpress (Molecular Devices) software.

2. Results on Neurite Lengthening

The results for neurite lengthening are shown in FIG. 10 for combinations 1, 2 and 4, and in FIG. 11 for combinations 3 and 4.

2.1 Influence of the Combination of Astragalosides and Polysaccharides

The results of Tests A and B show that combinations 1 and 2 enable lengthening of the neurites compared to the control. As a matter of fact, combination 1 enables neurite lengthening of about 16% in Test A and of about 26% in Test B, and combination 2 enables neurite lengthening of about 24% in Test A and of about 21% in Test B.

However, lengthening of the neurites obtained in the case of combination 1 (not comprising astragalosides) or combination 2 (not comprising polysaccharides) is less compared with the lengthening of the neurites obtained in the case of combination 4. As a matter of fact, combination 4 enables lengthening of the neurites by approximately 32% in Test A and even by approximately 40% in Test B.

Therefore, a combination of extracts comprising both astragalosides and polysaccharides makes it possible to obtain greater lengthening of the neurites than a combination of extracts comprising only one of these active ingredients.

2.2 Influence of Rosavin

The results of Tests A and B show that combination 3, which does not contain rosavin, enables lengthening of the neurites by about 5% in Test A and by approximately 8% in Test B, compared to the control.

However, the lengthening of the neurites obtained in the case of that combination 3 is appreciably less compared with the lengthening of the neurites obtained in the case of combination 4. As a matter of fact, combination 4 enables lengthening of the neurites by approximately 32% in Test A and even by approximately 40% in Test B.

Therefore, a combination of extracts comprising rosavin provides much greater lengthening of the neurites than a combination of extracts without rosavin.

The invention claimed is:

1. A method of treating or providing a neuroprotective effect against a neurodegenerative disease comprising administering a therapeutically effective amount of each of a dried extract of *Rhodiola rosea* and a dried extract of *Astragalus membranaceus* simultaneously, to an individual in need thereof, wherein the dried extract of *Rhodiola rosea* contains at least 1.5% by dry weight of rosavin with respect to the total weight of dried extract of *Rhodiola rosea*, and
   wherein the dried extract of *Astragalus membranaceus* comprises at least 0.2% by dry weight of astragalosides with respect to the total weight of dry extract of *Astragalus membranaceus* and at least 10% by dry weight of polysaccharides with respect to the total weight of dried extract of *Astragalus membranaceus*.

2. The method of claim 1, wherein the neurodegenerative disease is Alzheimer's disease.

3. The method of claim 1, wherein the neurodegenerative disease is Parkinson's disease.

4. The method of claim 1, comprising administering the dried extract of *Rhodiola rosea* at a dose of at least 50 mg/day.

5. The method of claim 1, wherein the dried extract of *Rhodiola rosea* contains at least 0.25% by dry weight of salidroside with respect to the total weight of dried extract of *Rhodiola rosea*.

6. The method of claim 1, comprising administering the dried extract of *Astragalus membranaceus* at a dose of 50 mg/day.

7. The method of claim 1, wherein the ratio by dry weight of the dried extract of *Astragalus membranaceus* relative to the dried extract of *Rhodiola rosea* is between 0.5 and 1.5.

8. The method of claim 1, further comprising administering tocopherol, selenium, silicon, zinc, magnesium, polyphenols other than those derived from the *Rhodiola rosea* and *Astragalus membranaceus* extracts, or mixtures thereof.

9. A method for elongating neurites of neurons comprising administering a therapeutically effective amount of each of an extract of *Rhodiola rosea* and an extract of *Astragalus membranaceus* simultaneously to an individual in need thereof,
   wherein the dried extract of *Rhodiola rosea*contains at least 1.5% by dry weight of rosavin with respect to the total weight of dried extract of *Rhodiola rosea*, and
   wherein the dried extract of *Astragalus membranaceus* comprises at least 0.2% by dry weight of astragalosides with respect to the total weight of dry extract of *Astragalus membranaceus* and at least 10% by dry weight of polysaccharides with respect to the total weight of dried extract of *Astragalus membranaceus*.

10. The method of claim 9, comprising administering the extract of *Rhodiola rosea* at a dose of at least 50 mg/day.

11. The method of claim 9, wherein the extract of *Rhodiola rosea* contains at least 0.25% by weight of salidroside with respect to the total weight of dry extract of *Rhodiola rosea*.

12. The method of claim 9, comprising administering the extract of *Astragalus membranaceus* at a dose of 50 mg/day.

* * * * *